(12) United States Patent
Toyoda

(10) Patent No.: US 6,781,098 B2
(45) Date of Patent: Aug. 24, 2004

(54) HEATER CONTROLLER FOR AN OXYGEN SENSOR

(75) Inventor: Katsuhiko Toyoda, Shizuoka-ken (JP)

(73) Assignee: Suzuki Motor Corporation, Shizuoka-ken (JP)

( * ) Notice: Subject to any disclaimer, the term of this patent is extended or adjusted under 35 U.S.C. 154(b) by 0 days.

(21) Appl. No.: 10/437,787

(22) Filed: May 14, 2003

(65) Prior Publication Data

US 2003/0213795 A1 Nov. 20, 2003

(30) Foreign Application Priority Data

May 15, 2002 (JP) ........................................ 2002-139945

(51) Int. Cl.$^7$ ............................. F02D 41/04; H05B 1/02
(52) U.S. Cl. ........................ 219/501; 219/497; 219/202; 219/492; 123/697; 374/132; 374/141
(58) Field of Search ................................ 219/497, 202, 219/490, 205, 492, 494, 508, 501; 123/697; 374/141, 132, 133, 109

(56) References Cited

U.S. PATENT DOCUMENTS

| | | | |
|---|---|---|---|
| 4,708,777 A | * | 11/1987 | Kuraoka .................. 205/784.5 |
| 5,036,820 A | * | 8/1991 | Fujimoto et al. ........... 123/686 |
| 5,353,775 A | | 10/1994 | Yamashita et al. |
| 5,656,190 A | | 8/1997 | Aoki |
| 6,192,678 B1 | * | 2/2001 | Tachibana ..................... 60/289 |
| 6,384,386 B2 | * | 5/2002 | Hashimoto et al. ......... 219/497 |

FOREIGN PATENT DOCUMENTS

| | | |
|---|---|---|
| JP | 05-202785 | 8/1993 |
| JP | 08-220059 | 8/1996 |
| JP | 11-218044 | 8/1999 |

* cited by examiner

*Primary Examiner*—Mark Paschall
(74) *Attorney, Agent, or Firm*—Flynn, Thiel, Boutell & Tanis, P.C.

(57) ABSTRACT

A heater controller for an oxygen sensor associated with a vehicle engine. The controller includes a start detect section, a restart determination section, and a heater delay control section. The start detect section detects whether the engine is started. The restart determination section determines whether the engine is restarted. The heater delay control section operates the heater to activate after a predetermined delay time, delayed from startup of the engine, that is set according to an engine water temperature. The operation of the heater is executed when the start detect section detects that the engine is started and the restart determination section determines that the engine is not restarted.

25 Claims, 13 Drawing Sheets

HEATER CONTROLLER FOR AN OXYGEN SENSOR

FIELD OF THE INVENTION

This invention relates to heater controllers for oxygen sensors, and more particularly to a heater controller for an oxygen sensor associated with a vehicle engine and provided with a heater to maintain the oxygen sensors in a preferable activated state.

BACKGROUND OF THE INVENTION

In engines for vehicles, oxygen (exhaust) sensors are provided in the exhaust system to control air-fuel ratio based on measured concentrations of oxygen in the exhaust gas for feedback. Some oxygen sensors are provided with heaters to maintain elements in a preferable activated state. The heaters are operated by controllers so as to be turned on at 100% of duty value and turned off at 0% of duty value.

Examples of heater controllers for oxygen sensors are disclosed in, e.g., JP Laid-Open Nos. H11-218044, H08-220059, and H05-202785.

According to JP Laid-Open H11-218044, a heater is energized when an ignition switch is turned on, and its duty is controlled according to both engine load and elapsed time after turning on the ignition switch so that the oxygen sensor reaches appropriate temperature quickly.

According to JP Laid-Open H08-220059, heater resistance is guarded at a higher first value in heating for maintaining the sensor in the preferable activated state, and is guarded at a second value that is lower than the first value after completion of the warming up of the air-fuel ratio sensor.

According to JP Laid-Open H05-202785, a heating sensor element is heated by setting a target element temperature to a high level if the engine temperature is relatively low, or by setting the target element temperature to a relatively low level if the cooling water temperature is relatively high.

In the conventional heater controller for the oxygen sensor according to, e.g. JP H11-218044, the heater for the oxygen sensor is controlled when the engine starts, that is the heater is energized when the ignition switch is turned on. The heater is controlled firstly according to the engine load, secondly by a map of engine speed and engine load, thirdly by the intake temperature and fourthly by elapsed time. The heater is controlled not only when the ignition switch is turned on to energize the heater, but even if the engine is started and the heater is energized, the above-mentioned first to fourth conditions are satisfied.

Moreover, the heater is energized at the instant when the ignition switch is turned on or the engine is started. As shown in FIG. 6 of JP Laid-Open H11-218044, the duty value for the heater is set as high as possible to expedite the activation of the oxygen sensor. However, condensation can form inside the exhaust system until the temperature of the exhaust system toward the upstream side of the oxygen sensor becomes about 50° C. Exposing the oxygen sensor element that is heated by the heater to moisture can undesirably effect or damage the oxygen sensor element. Generally, if the temperature of the oxygen sensor element increases over 300° C. before the temperature of the exhaust system toward the upstream side of the oxygen sensor reaches about 50° C., then the condensation or moisture can damage the oxygen sensor element upon contact therewith. Accordingly, it is conventional to permit the heater to be energized instantly after the engine starts only if the engine water temperature is over about 20° C.

Further, the heater is not conventionally energized when the engine water is at a low temperature to avoid damage to the oxygen sensor element. However, if the heater is not energized at all, the activation of the oxygen sensor is delayed. Feed back control for fuel is not executed until the oxygen sensor is activated, so that the fuel is injected under base control. Since the air-fuel ratio is generally set toward a rich mixture until the engine water temperature is increased after the engine starts, the efficiency of purification of the catalyst or catalytic converter is reduced and emits much undesirable exhaust gas that is not purified by the catalyst.

Still further, in the prior heater control, the heater is prevented from being energized so as to avoid damaging of the element. This delays the activation of the oxygen sensor. Output of emissions or exhaust gas is undesirably increased when the engine is started with a low temperature of the engine water (i.e. coolant). Depending on the construction of the engine exhaust system, when the exhaust system temperature is over a predetermined value (EXTL) (i.e. about 50° C.), moisture inside the components of the exhaust system is evaporated, and the oxygen sensor is not damaged and allows the heater to be energized.

Figure 14:
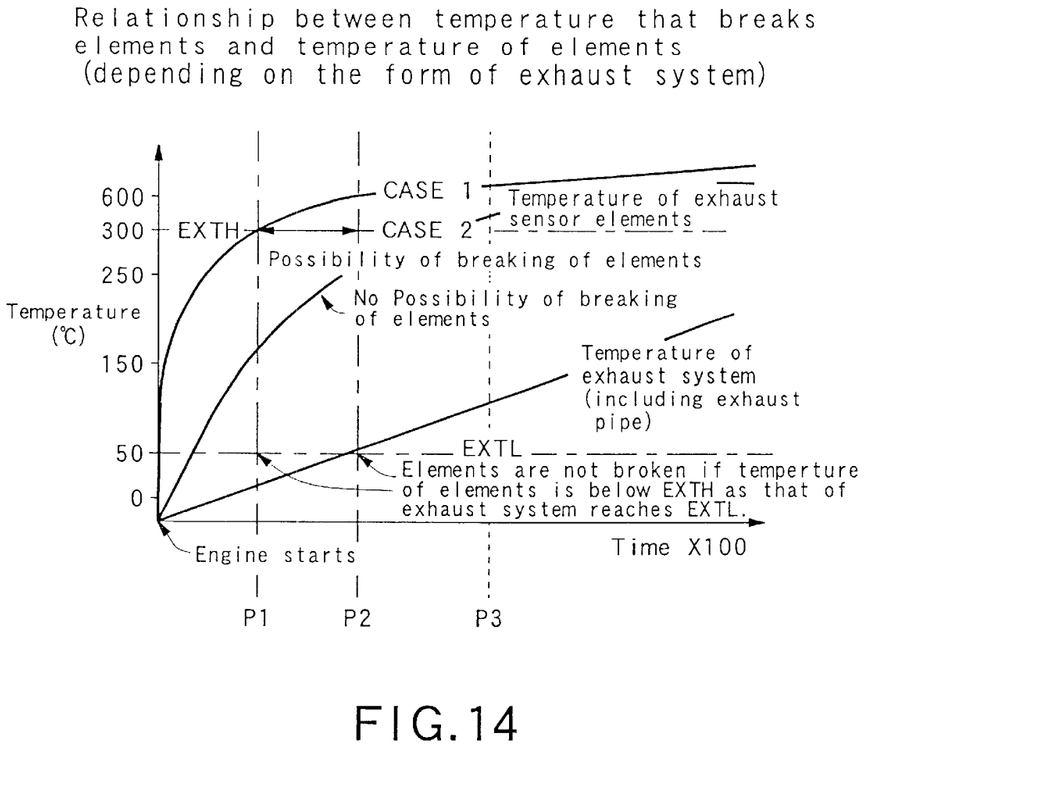
FIG. 14 is a time chart showing conventional relationship of the temperatures in which an exhaust sensor element is broken.

More particularly, as shown in FIG. 14, for CASE 1 showing the temperatures of the oxygen (exhaust) sensor element, when the temperature of the exhaust sensor element is higher than that of a predetermined value EXTH (about 300° C.) (P1) before the temperature of the exhaust system (including exhaust pipe) increases to a predetermined value EXTL (about 50° C.), the oxygen sensor element may be damaged. In other words, moisture on the sensor element can damage the sensor element when the temperature of the exhaust system is below the predetermined value EXTL (about 50° C.) and when the temperature of the exhaust sensor is higher than the predetermined value EXTH (about 300° C.). For CASE 2, the sensor element temperature is lower than the predetermined value EXTH (about 300° C.) when the temperature of the exhaust system reaches the predetermined value EXTL (about 50° C.) (P2), and is higher than the value EXTH (about 300° C.) when the exhaust system temperature is higher than the value EXTL (about 50° C.) (P3), thereby preventing moisture and the resulting damage to the sensor element.

Figure 15:
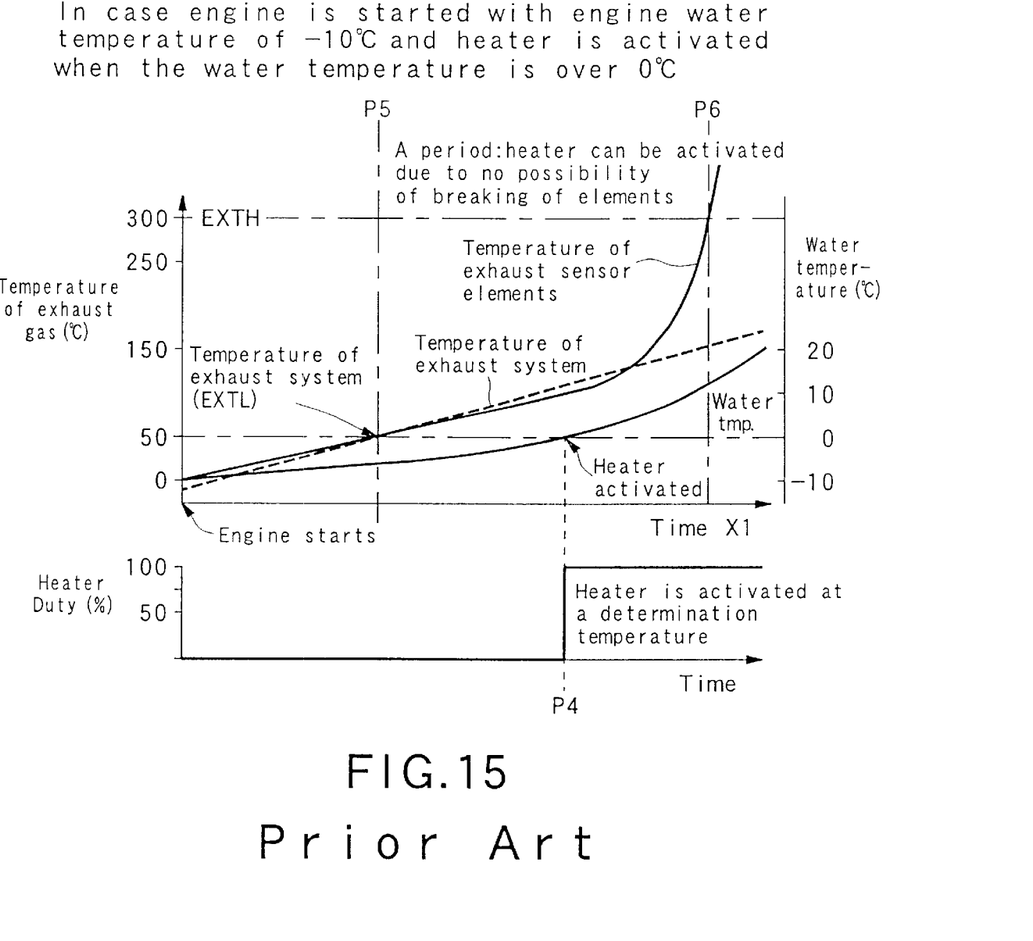
FIG. 15 is a time chart wherein the engine is started at −10° C. and the heater is activated at a temperature of engine water over 0° C.

FIG. 15 illustrates a conventional control of a heater according to the engine water (i.e. coolant) temperature. The heater is not energized at temperatures between the engine water temperature of −10° C. at startup of the engine and an engine water temperature (0° C.) at which the heater is turned on (P4). The engine water temperature is hardly increased at startup of the engine. During the time period (P5 to P6) when the exhaust system reaches the desired temperature (i.e., 50° C. or above), the heater is not energized even if it could be. The oxygen sensor is not activated during this period, and the feed back of the air-fuel ratio is not executed, thereby increasing the output of the undesirable exhaust gases. Also, the lower the engine water temperature at startup, the longer the time for the exhaust system temperature to reach the predetermined value (EXTL; i.e. about 50° C.), and the longer the time for the exhaust system temperature to reach a heater energy start temperature (i.e. 50° C.). The heater is not energized in this case, which increases the period of time that the exhaust gas is emitted, and feed back control of the air-fuel ratio is delayed thereby decreasing exhaust purification efficiency.

BRIEF SUMMARY OF THE INVENTION

To obviate or at least minimize the above inconveniences, the present invention provides a heater controller and control method for an oxygen sensor which detects concentrations of oxygen in exhaust gas from a vehicle engine and is controlled by a heater which has its duty (i.e., its electrical energization) controlled. The controller includes a start detect section, a restart determination section, and a heater delay control section. The start detect section detects whether the engine is started. The restart determination section determines whether certain parameters or conditions have been reached, that commonly indicate that the engine was recently restarted. The heater delay control section operates the heater to activate after a predetermined delay time, delayed from startup of the engine, that is set according to engine water temperature when the start detect section detects that the engine is started and when the restart determination section determines that the engine restart parameters have not been reached, also referred to as "not restarted."

According to the present invention, the heater is activated after the predetermined delay time that is set according to the engine water temperature after startup of the engine when it is determined that the engine is not restarted. That is, the delay time is set according to the engine water temperature at startup of the engine. Start of the heater control is delayed from the startup of the engine, which can also be set not according to the engine water temperature but according to a warm up state of the engine. The activation of the oxygen sensor is achieved at an early stage without damaging the structure thereof. The feed back control of the air-fuel ratio is achieved at an early stage to prevent increases in the exhaust gas output and thus improve the efficiency of exhaust gas purification.

DETAILED DESCRIPTION OF THE INVENTION

Embodiments of the present invention will now be described in detail with reference to the drawings.

Figure 10:
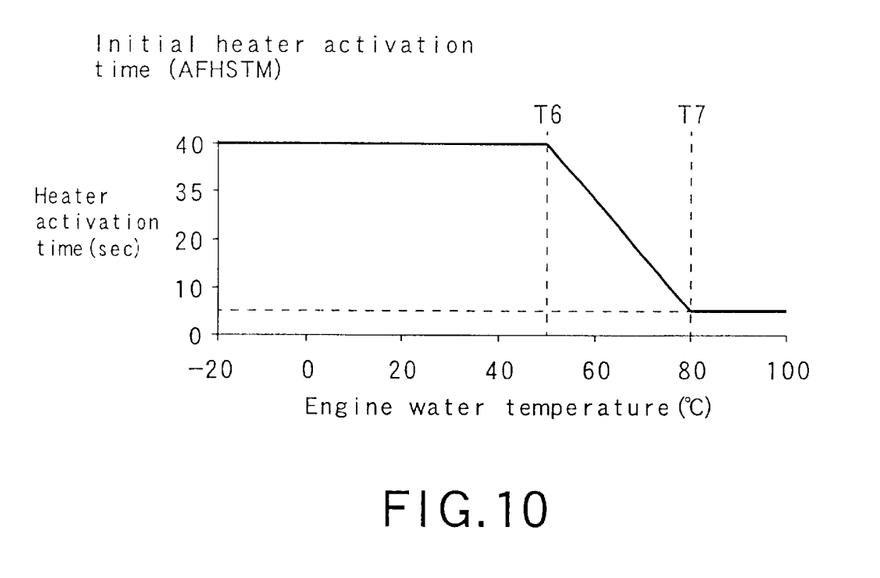
FIG. 10 is a graph for initial heater activation time.
Figure 11:
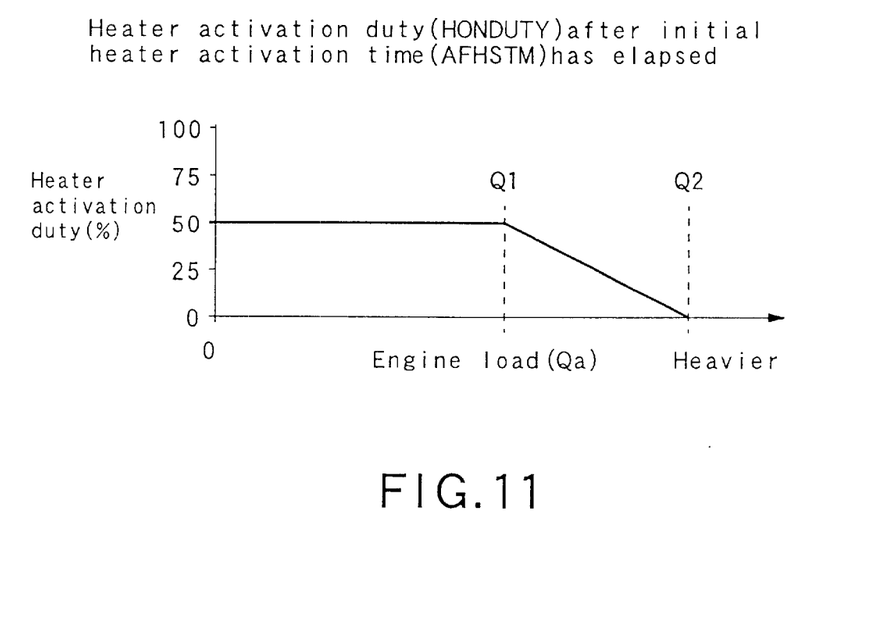
FIG. 11 is a graph for heater duty value after the initial heater activation time has elapsed.
Figure 12:
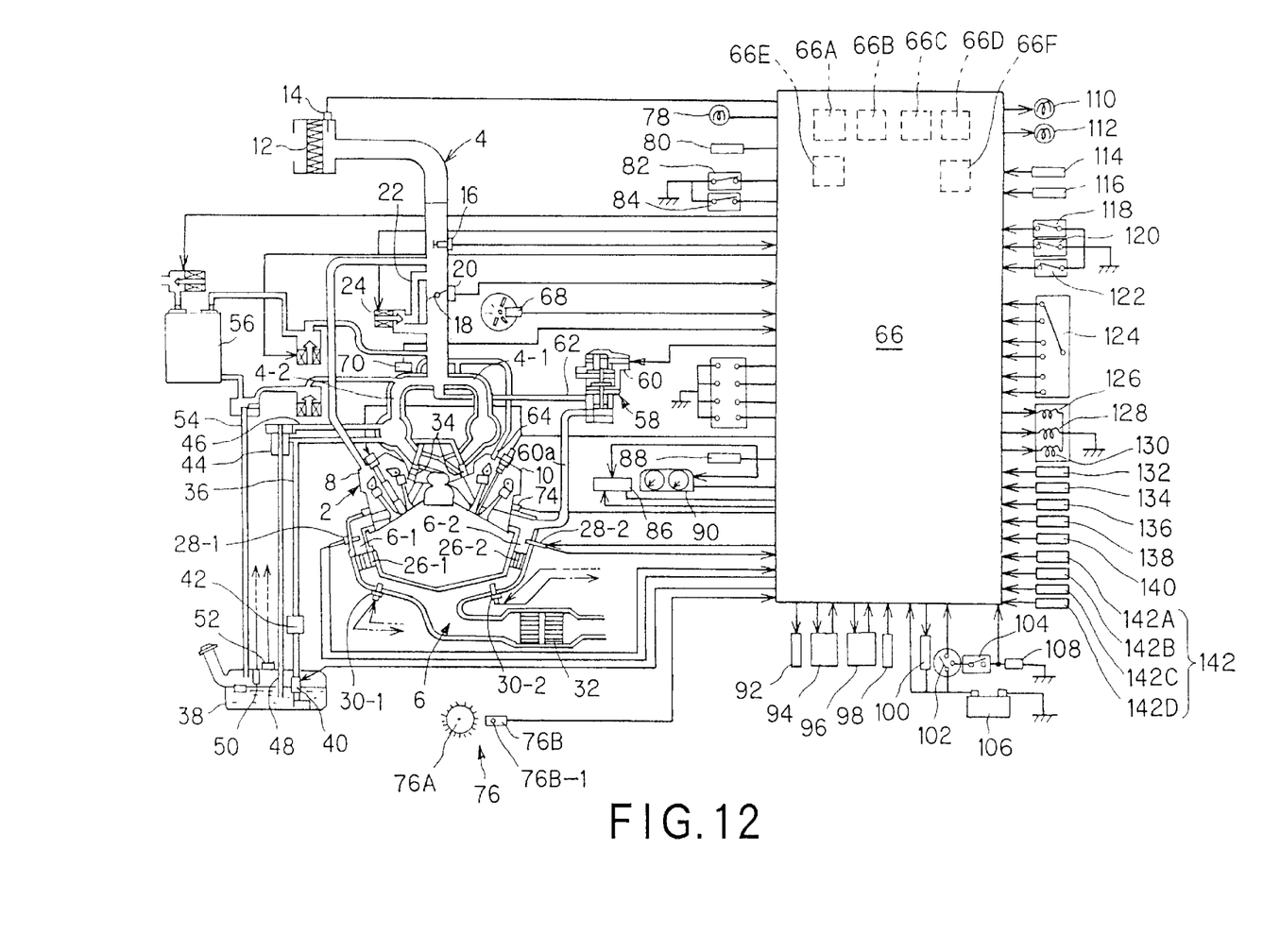
FIG. 12 is a diagram of a heater controller for the oxygen sensors.

FIGS. 1–12 illustrate an embodiment of the present invention. In FIG. 12, a vehicle (not shown) includes an engine 2 mounted thereon, an intake passage 4, and an exhaust passage 6. In the illustrated embodiment the engine 2 has first and second cylinder banks 8, 10 formed in a V-shape.

The intake passage 4 is provided with, from upstream thereof, an air cleaner 12, an intake temperature sensor 14 to detect temperature of intake air, an airflow sensor 16 to detect quantity of intake air, and a throttle valve or plate 18. Down stream the intake passage 4 is divided into two intake branch passages 4-1, 4-2. The intake branch passage 4-1 is connected to combustion chambers (not shown) in the first cylinder bank 8, and the branch passage 4-2 is connected to the combustion chambers in the second cylinder bank 10.

In the intake passage 4, a throttle-opening sensor 20 is disposed to detect opening degree of the throttle valve 18. The intake passage 4 includes a bypass 22 to avoid the throttle valve 18. An idle control valve (ISC valve) 24 is positioned in the bypass 22 to adjust air quantity.

An exhaust passage 6 is divided into first and second exhaust branch passages 6-1, 6-2 on an upstream side thereof. The exhaust branch passage 6-1 is connected to the combustion chambers in the first cylinder bank 8, and the passage 6-2 is connected to the combustion chambers in the second cylinder bank 10.

The exhaust branch passages 6-1, 6-2 include catalytic converters 26-1, 26-2 respectively. Toward an upstream side of the first exhaust branch passage 6-1 with respect to the catalytic converter 26-1, a first front oxygen (i.e. exhaust gas) sensor 28-1 is disposed to detect concentrations of oxygen in the exhaust gas in the branch passage 6-1. Toward a lower or down stream side of the branch passage 6-1 with respect to the catalytic converter 26-1, a first rear oxygen (exhaust) sensor 30-1 is disposed.

Toward an upstream side of the second exhaust branch passage 6-2 with respect to the catalytic converter 26-2, a second front oxygen (i.e. exhaust gas) sensor 28-2 is disposed to detect concentrations of oxygen in the exhaust gas in the branch passage 6-2. Toward a lower or down stream side of the branch passage 6-2 with respect to the catalytic converter 26-2, a second rear oxygen (exhaust) sensor 30-2 is disposed.

Downstream of the rear oxygen (exhaust) sensors 30-1, 30-2, the exhaust branch passages 6-2, 6-2 are joined, and a three-way catalytic converter 32 is disposed downstream from the joined portion.

In the engine 2, fuel injection valves 34 are oriented to the combustion chambers. The fuel injection valves 34 are connected to a fuel tank 38 through a fuel feed passage 36. A fuel pump 40 pumps fuel from the fuel tank 38 through a fuel filter 42 for supply to the fuel injection valves 34 through the fuel feed passage 36.

In the fuel feed passage 36, a fuel pressure regulator 44 is disposed to adjust the pressure of the fuel. The fuel regulator 44 adjusts the fuel pressure to a certain value by an intake pipe pressure that is introduced from a pressure introduction passage 46 that is connected to the intake passage 4. Excess fuel is returned to the fuel tank 38 through a fuel return passage 48. The fuel tank 38 is provided with a fuel level sensor 50 and a pressure sensor 52.

The fuel tank 38 is communicated with the downstream portion of the intake passage 4, downstream of the throttle valve 18, through an evaporated fuel passage 54. The evaporated fuel passage 54 has a canister 56 therein.

The engine 2 is provided with an EGR controller 58 that includes an EGR valve 60 to control the quantity of exhaust gas recycling from the exhaust system to the intake system. The EGR valve 60 communicates through a passage 60a with the first exhaust branch passage 6-2 upstream of the second front oxygen sensor 28-2, and with an EGR passage 62 that connects to the intake at a junction of the first and second intake branch passages 4-1, 4-2 so as to electronically control the quantity of exhaust gas which is fed back to the intake passage.

A PCV valve 64 is provided in the second cylinder bank 10 of the engine 2.

A controller (ECM) 66 is connected to the intake temperature sensor 14, the mass airflow sensor 16, the throttle opening degree sensor 20, the idle control valve 24, the first front and rear oxygen (exhaust) sensors 28-1, 30-1, the second front and rear oxygen (exhaust) sensors 28-2, 30-2, the fuel injection valve 34, the fuel pump 40, the pressure sensor 52, and the EGR valve 60.

The controller 66 is also connected to: a cam angle sensor 68 to output a signal of measured rotating degree of the camshafts (not shown) of the engine 2; a intake pressure sensor 70 to detect pressure in the intake pipe or intake pressure; an ignition coil assembly (not shown); a water temperature sensor 74 to detect the engine water (i.e. coolant) temperature; a crank angle sensor 76 to output signal of measured rotating angle of a crankshaft (not shown) of the engine 2; an indicator lamp 78; a connection terminal 80; a switch for pressure of a power steering 82; a switch for a heater blower fan 84; a cruise control module 86; a vehicle speed sensor 88 to detect speeds of the vehicle; a combination meter 90; an A/D condenser fan relay 92; an A/C controller 94; a data link connector 96; an ABS controller module 98; a main relay 100; an ignition switch 102 to output signal when an engine key is turned; a P/N position switch 104; a battery 106; a starter switch 108 that is turned on to output signal when a starter is activated; an O/D off lamp 110; a power lamp 112; a light switch 114; a stop lamp switch 116, an O/D cut switch 118; a power/normal change switch 120; a 4WD LOW switch 122; a transmission range switch 124; first and solenoid valves 126, 128; a TCC solenoid valve 130; an A/T input speed sensor 132; an A/T output speed sensor 134; an idle switch 136 that is turned on when the engine 2 is idling; an engine speed sensor 138 to detect engine speed; and an exhaust system temperature sensor 140 to detect temperature of the exhaust system of the engine 2.

A heater 142 for the oxygen sensors 28-1, 28-2, 30-1, 30-2 includes a first front heater 142A installed in the first front oxygen (exhaust) sensor 28-1, a first rear heater 142B installed in the first rear oxygen (exhaust) sensor 30-1, a second front heater 142C installed in the second front oxygen (exhaust) sensor 28-2 and a second rear heater 142D installed in the second rear oxygen (exhaust) sensor 30-2. The controller 66 controls each heater 142 in the range of its duty value (0–100%), i.e., its range of electrical energization. That is, the heater is turned on at the duty value of 100% and is turned off at 0% to manage the temperatures of the respective oxygen sensors so that the oxygen sensor elements are activated in a preferred state.

The controller 66 executes feed back control based on concentrations of oxygen in the exhaust gas as detected by the oxygen sensors.

The controller 66 includes a start detect section 66A, a restart determination section 66B, and a heater delay control section 66C. The start detect section 66A determines whether the engine 2 is started. The restart determination section 66B determines whether the engine 2 is restarted. The heater delay control section 66C operates to turn on the heaters 142 for the oxygen (exhaust) sensors after a predetermined delay time (HDLY) that is set according to the engine water temperature after startup of the engine 2 when the start detect section 66A detects that the engine 2 is started and when the restart detect section 66B determines that the engine 2 is not restarted.

Figure 4:
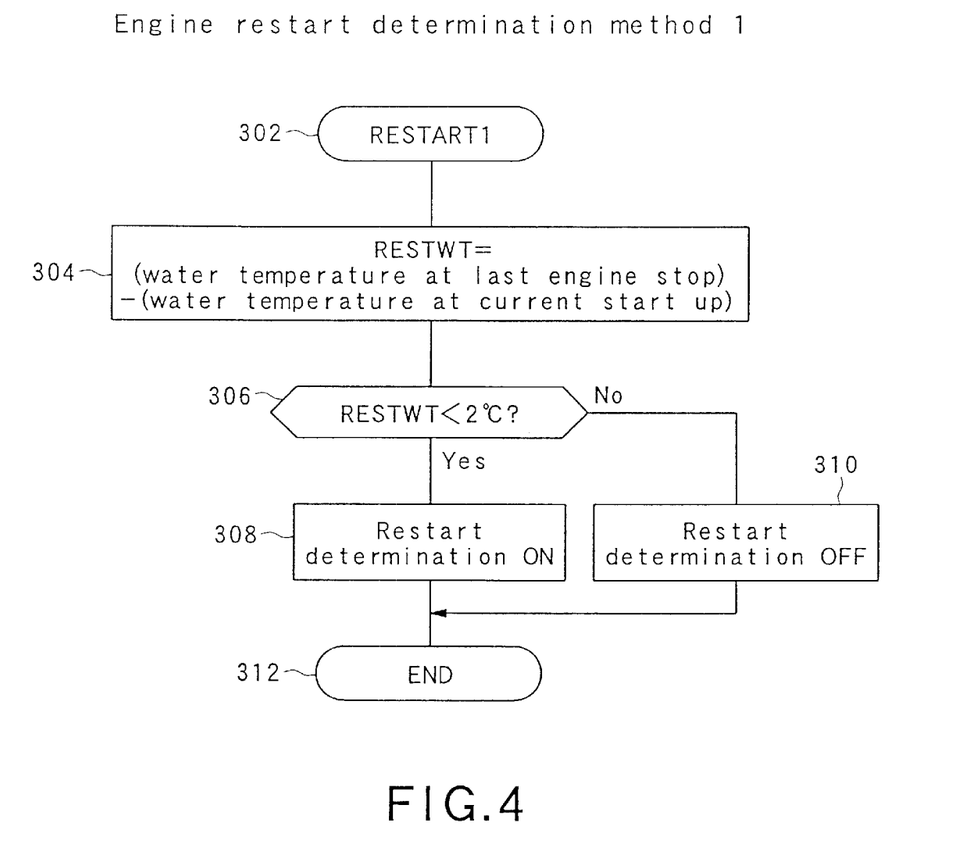
FIG. 4 is a flow chart to determine whether the engine is restarted according to a first variation of the invention.
Figure 5:
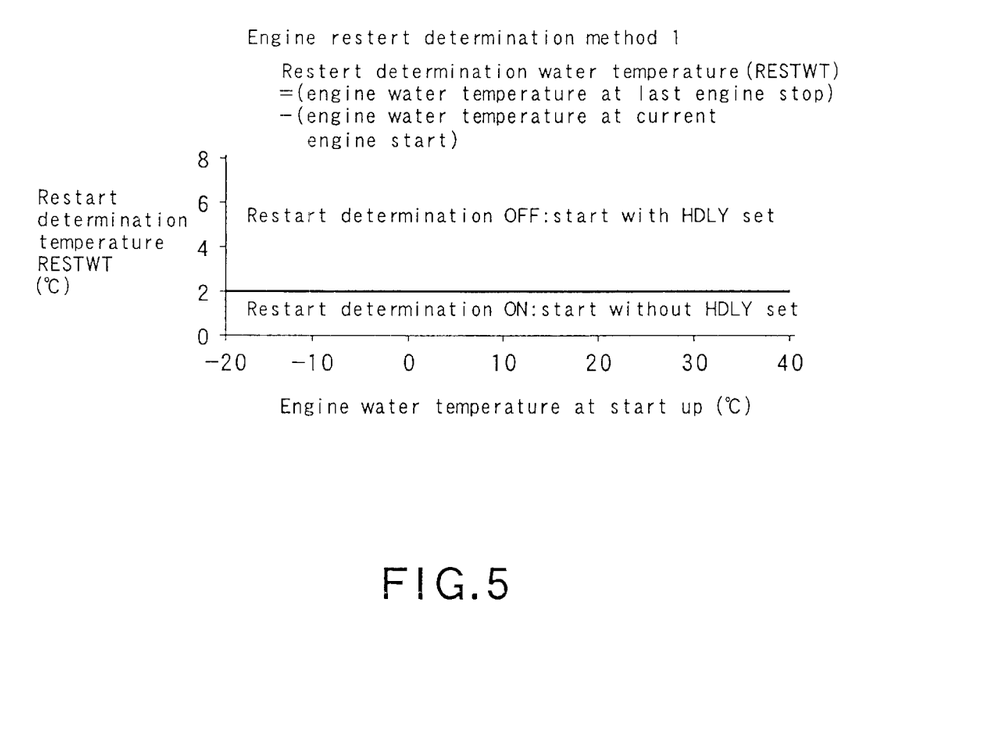
FIG. 5 is a table for a restart determination water temperature at restart of the engine in the first variation.
Figure 6:
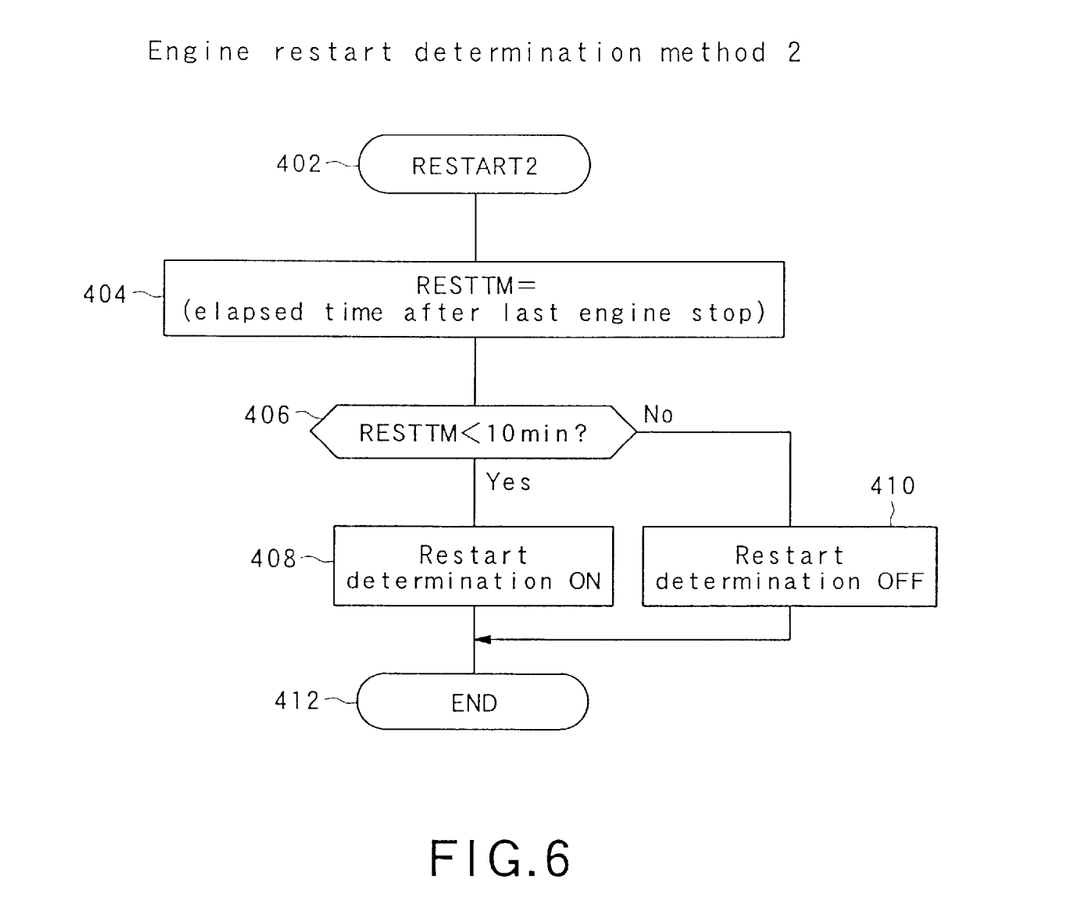
FIG. 6 is a flow chart to determine whether the engine is restarted according to a second variation of the invention.
Figure 7:
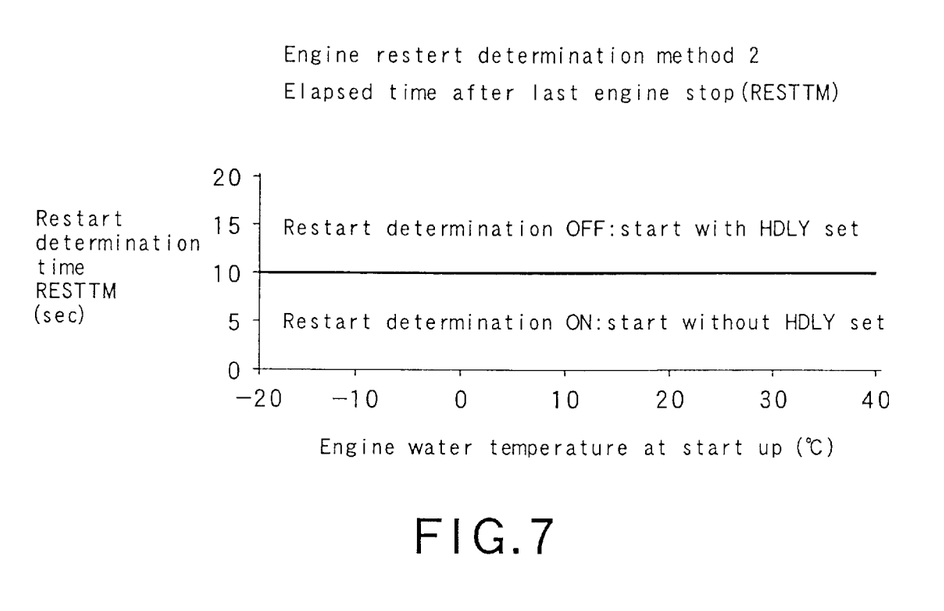
FIG. 7 is a table for a restart determination time at restart of the engine according to the second variation.

The restart determination section 66B determines whether the engine 2 is restarted by a first method as shown in FIGS. 4 and 5 or by a second method as shown in FIGS. 6 and 7.

With respect to the first decision method (FIGS. 4 and 5) to determine if the engine 2 is restarted, the restart determination section 66B decides that engine 2 is restarted when a temperature differential between the engine water temperature at the most recent engine shut-off (also referred to as the engine water temperature at engine stop of last time), and the engine water temperature at the next engine startup is less than a predetermined comparison temperature (e.g. 2° C.). More particularly, as shown in FIGS. 4–5, when a program starts (RESTART 1) at step 302, a restart determination water temperature (RESTWT) is calculated at step 304 from an equation wherein RESTWT="the engine water temperature at last engine stop"—"the engine water temperature at current engine startup". Then a determination is made at step 306 as to whether the restart determination water temperature (RESTWT) is less than the comparison temperature (e.g. 2° C.). If the determination at step 306 is "Yes", it is determined that the engine 2 is restarted (restart determination ON) at step 308. However, if the determination is "No", it is determined that the engine 2 is not restarted (restart determination OFF) at step 310. The program ends at step 312 after the determinations are made at steps 308 or 310. That is, as shown in FIGS. 4–5, this control method presumes a reduction in the temperature of the exhaust system based on the temperature differential between the engine water temperature at the last engine stop and the current engine startup. The reduction in temperature of the exhaust system is low when the water temperature differential is small, which means there is no moisture in the exhaust system component. Accordingly, there is no possibility of condensation forming on the oxygen sensors 28-1, 28-2, 30-1, 30-2 at restart of the engine 2. The heater 142 can be energized at the instant the engine 2 is restarted without setting the delay time (startup without HDLY set; FIG. 5).

With respect to the second decision method (FIGS. 6 and 7), the restart determination section 66B determines that the engine 2 is restarted when the elapsed time after the last shut-off or stop page of the engine 2 is shorter than a predetermined comparison time (e.g. 10 minutes). More particularly, as shown in FIGS. 6–7, the program starts at step 402 (engine RESTART 2). An elapsed time after the last stop of the engine (RESTTM) is set at step 404. Then a determination is made at step 406 whether the elapsed time (RESTTM) is shorter than the comparison time (e.g. 10 minutes). If the determination at step 406 is "Yes", then it is determined that the engine 2 is restarted (restart ON) at step 408. However, if the determination at step 406 is "No", then it is determined that the engine 2 is not restarted (restart OFF) at step 410. The program ends at step 412 after the determinations are made at steps 408 and 410. In this second determination method, similarly to the first method, the heater 142 can be instantly energized without setting the delay time after restart of the engine 2 (start without HDLY set; FIG. 7) when the elapsed time after the last engine stop is short.

Figure 8:
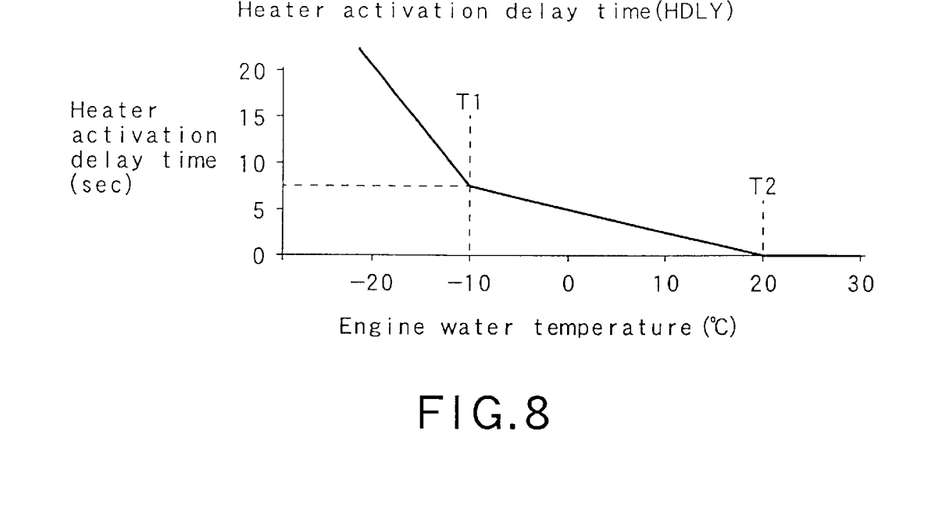
FIG. 8 is a graph for heater activation delay time.

Now referring to FIG. 8, the controller 66 is provided with a table to which a heater activation delay time (HDLY seconds) is allocated to delay activation of the heater 142 by a predetermined delay time after the engine start. In the table in FIG. 8, the heater activation delay time (HDLY) is set to steeply decrease as the water or coolant temperature increases about from −20° C. to about −10° C. (T1). At a temperature of about −10° C. (T1), the delay time (HDLY) is set at about 7.5 seconds. As the water temperature increases from about −10° C. to about +20° C. (T2), the delay time (HDLY) is gradually decreased. At a water temperature of about 20° C. (T2), the delay time (HDLY) becomes zero. In other words, as illustrated by the time chart of FIG. 2, the activation of the heater 142 is delayed by the predetermined time (S1) after the start of the engine 2 so that the temperature of the oxygen sensors becomes above a predetermined value for the sensors (EXTH; about 300° C.) after the temperature of the exhaust system reaches a predetermined value for the exhaust system (EXTL; about 50° C.).

Figure 3:
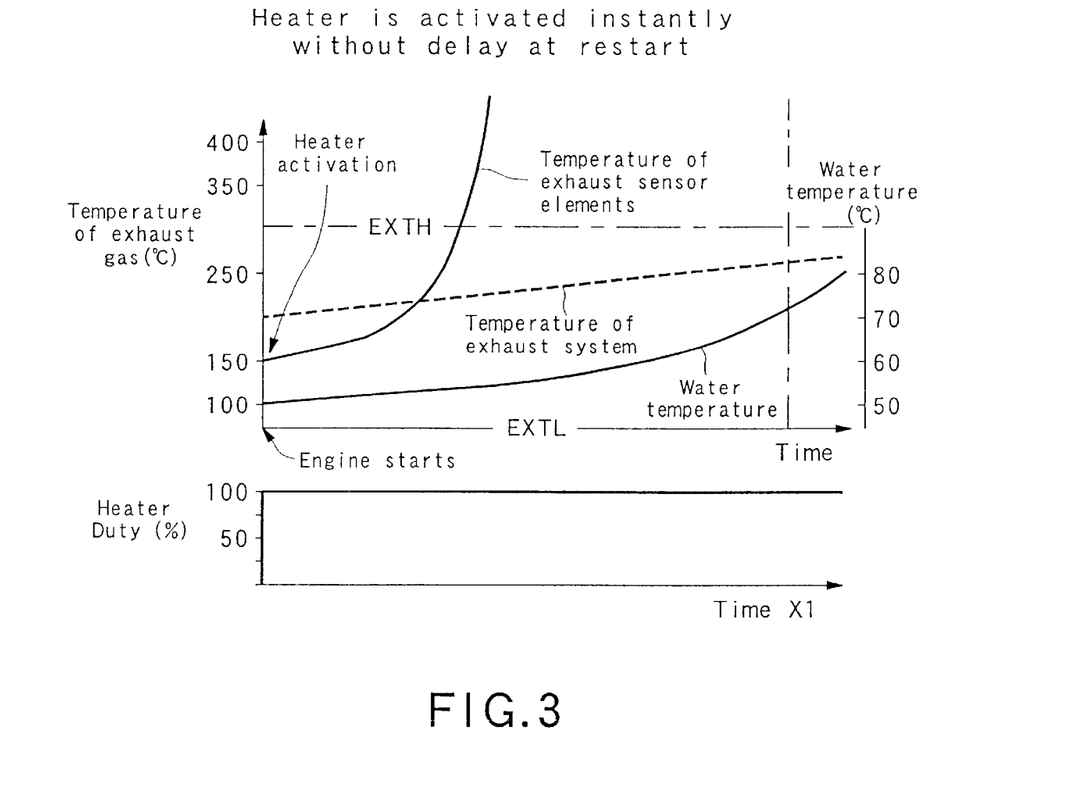
FIG. 3 is a time chart in which the heater is instantly turned on without a heater activation delay time at restart of the engine.

As illustrated by the time chart of FIG. 3, the controller 66 permits the heater 142, FIG. 12, to be energized instantly (ON) at restart of the engine 2, since the temperature of the exhaust system is still high even after the engine 2 is stopped, and there is no moisture in the exhaust system. Accordingly, the oxygen sensors can be quickly activated and the emission of exhaust gas can be reduced by feed back thereof to the incoming air-fuel ratio.

Figure 9:
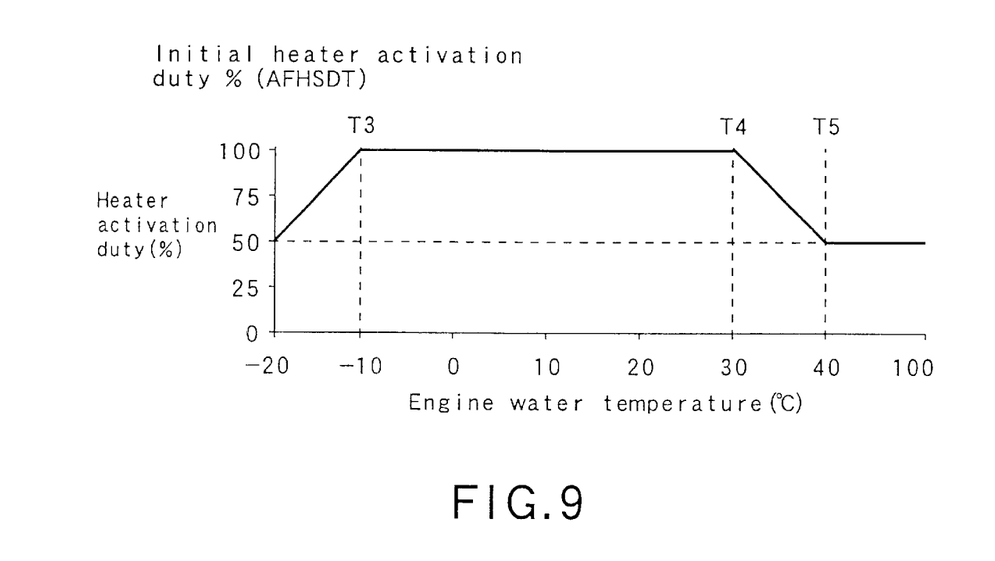
FIG. 9 is a graph for heater duty value on initial heater activation.

Further, the controller 66 has a heater control section 66D to activate the heater 142 according to a predetermined duty value (%) thereof based on the engine water temperature when the start detection section 66A detects the start up of the engine 2 and the restart determination section 66B determines the restart of the engine 2. As shown in FIG. 9, the controller 66 is provided with a table to which a heater activation duty value (AFHSDT) for an initial idle driving of the engine 2 is allocated according to the engine water temperature. In the table in FIG. 9, the heater activation duty value (AFHSDT) is set at about 50% when the engine water temperature is at a temperature of −20° C. As temperature of the engine water changes from about −20° C. to about −10° C. (T3), the duty value (AFHSDT) gradually increases from 50% to 100%. The duty value (AFHSDT) is at 100% at an engine water temperature of about −10° C. (T3). As the engine water increases from about −10° C. to about +30° C. (T4), the duty value (AFHSDT) is maintained constantly at 100%. Then the duty value (AFHSDT) gradually decreases from 100% to about 50% as the water temperature changes from about +30° C. to about +40° C. (T5). At water temperatures exceeding about 40° C., the duty value (AFHSDT) is maintained constantly at about 50%.

Referring now to FIG. 10, the controller 66 is provided with a table to which an initial heater activation time (AFHSTM) is allocated according to the engine water temperature. In the table in FIG. 10, at an engine water temperature of about −20° C., the initial heater activation time (AFHSTM) is set at about 40 seconds. As engine water temperature increases from about −20° C. to about +50° C. (T6), the activation time (AFHSTM) is maintained constantly (i.e., at about 40 seconds). As the water temperature increases from about 50° C. to about 80° C., the activation time (AFHSTM) decreases steeply (i.e. from 40 seconds), so that at a water temperature of about 80° C. (T7) the activation time (AFHSTM) is set for about 5 seconds. At water temperatures exceeding 80° C., the activation time (AFHSTM) is maintained constant (i.e. about 5 seconds).

Referring to FIG. 11, the controller 66 is provided with a table to which a heater activation duty value (HONDUTY), after elapsing of the initial heater activation time (AFHSTM), is allocated based on an engine load. In the table in FIG. 11, under an engine load of zero, the heater activation duty value (HONDUTY) after elapsing of the initial heater activation time (AFHSTM) is set at about 50%. Under an engine load between zero and a first load value (Q1), the duty value (HONDUTY) is maintained constant, i.e. at about 50%. After the engine load exceeds the first value (Q1), the duty value (HONDUTY) gradually decreases from the initial constant value (i.e. 50%). Under an engine load of a second load value (Q2) that is larger than the first load value (Q1), the duty value (HONDUTY) is set at zero %.

In other words, if the temperature of the oxygen sensors is increased by the temperature of the exhaust system resulting from the vehicle running, even after the engine is restarted and during the initial heater activation time (AFHSTM), then the heater 142 is activated according to the initial heater activation time (AFHSTM) as shown in FIG. 11.

The controller 66 includes a timer 66F, and an engine load detector 66E to detect the engine load from the throttle opening degree and the negative pressure in the intake pipes.

Next, the operation of the above-described invention is explained with reference to the flowchart in FIG. 1.

Figure 1:
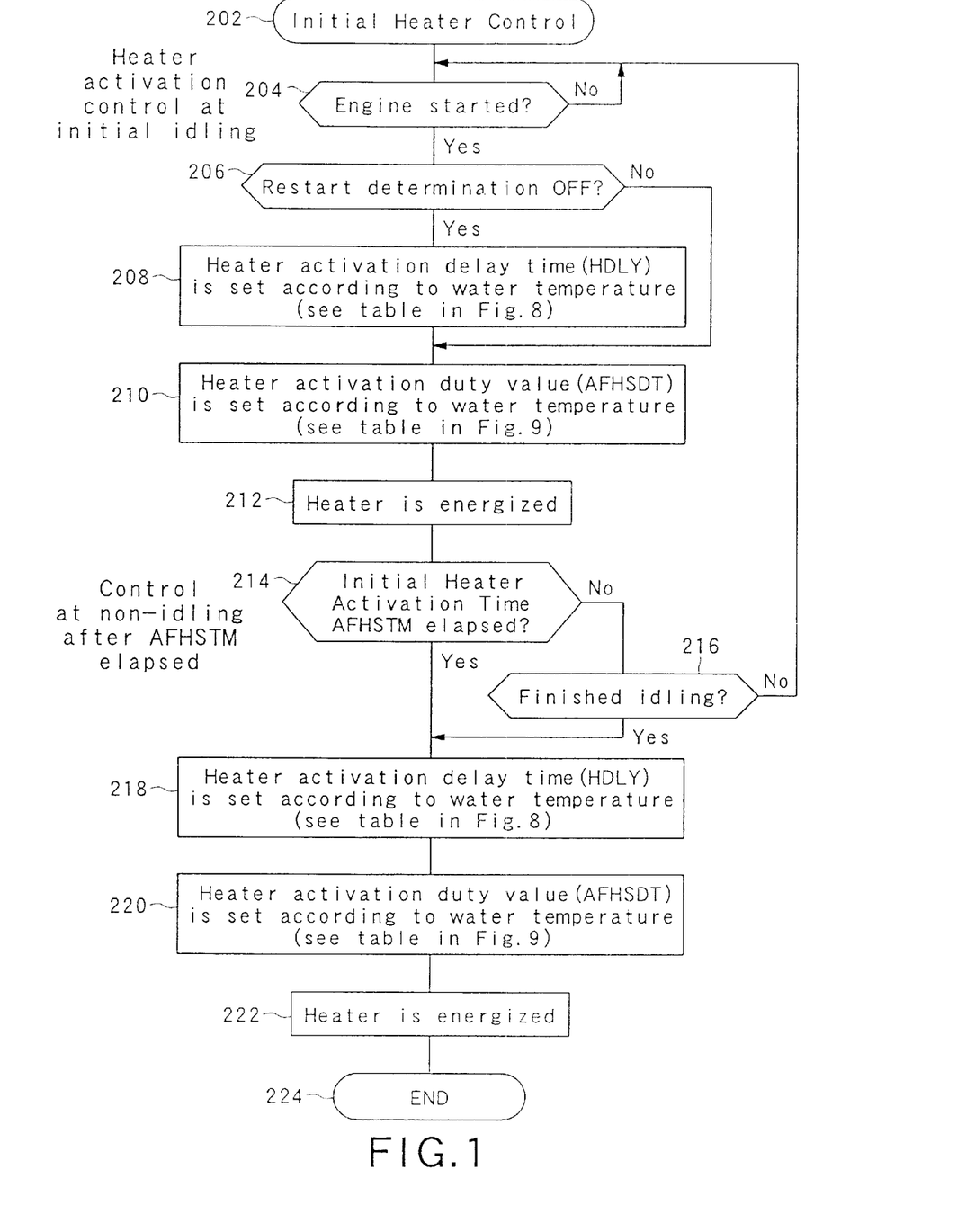
FIG. 1 is a flow chart illustrating a heater control for an oxygen sensor.
Figure 2:
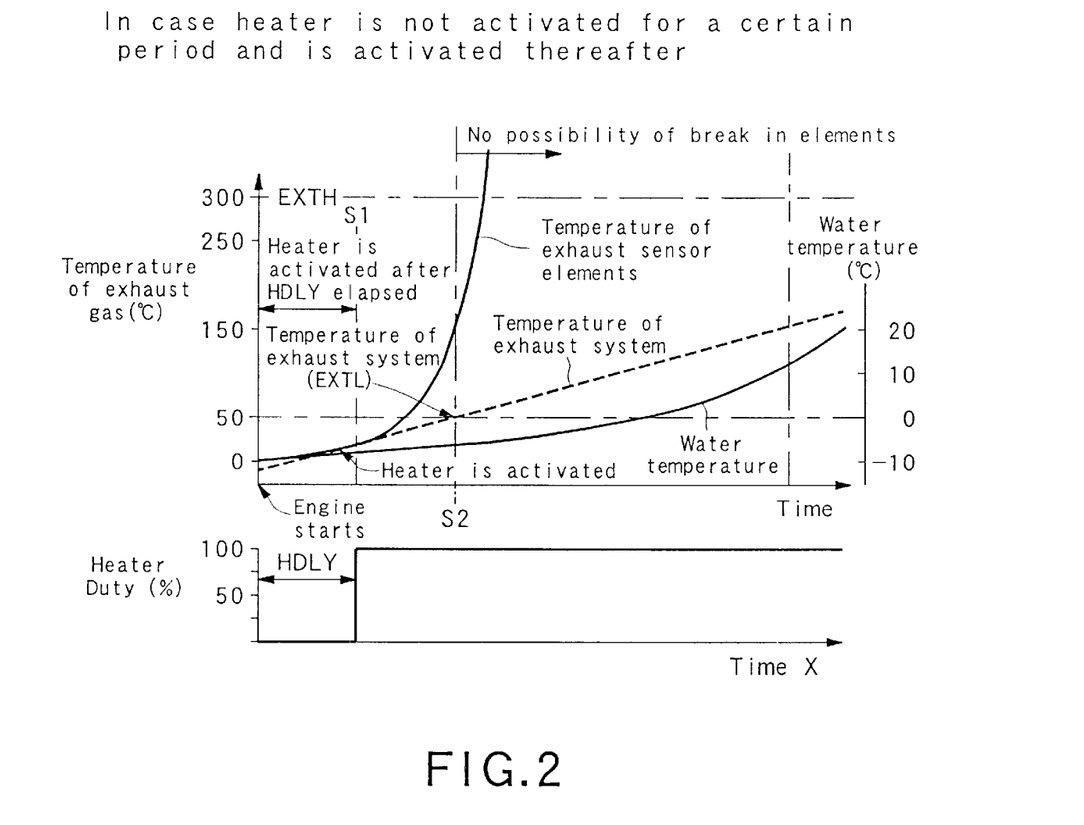
FIG. 2 is a time chart after an engine is started, and a heater is not activated for a certain period thereafter and is then activated.

In FIG. 1, the controller (i.e. controller 66 of FIG. 12) controls initial activation of the heater when the engine is at idle. The program for initial heater activation control starts at step 202. Then a determination is made at step 204 whether the engine 2 is started. If the determination is "No", the program goes back to step 204.

If the determination at step 204 is "Yes", then the determination is made at step 206 as to whether the engine 2 is restarted. If the determination at step 206 is "Yes" (restart OFF, i.e., the engine 2 is not restarted), then the heater activation delay time (HDLY) is set at step 208 according to the engine water temperature as shown in FIG. 8.

After the process at step 208 is finished or if the determination at step 206 is "No", then the heater activation duty value (AFHSDT) is set at step 210 according to the engine water temperature.

The heaters 142 are energized (turned on) at each set value at step 212. Then a determination is made at step 214 whether the initial heater activation time (AFHSTM) based on the engine water temperature has elapsed as shown in FIG. 10. If the determination at step 214 is "No", then a determination is made at step 216 whether the engine 2 is at idle. If the determination is "No", the program goes back to step 204. The control by the initial heater activation time (AFHSTM) at idle of the engine 2 is canceled after the initial heater activation time has elapsed or after the engine is not at idle.

If the determination at step 214 is "Yes" (AFHSTM has elapsed) or at step 216 is "Yes" (the engine 2 is not at idle), the control by the initial heater activation time at engine idling is canceled, so that the heater activation delay time (HDLY), as shown in FIG. 8, is again set based on the engine water temperature at step 218.

After the process at step 218, the initial heater activation duty value (AFHSDT) is set at step 220 based on the engine water temperature, as shown in FIG. 9.

The heaters 142 are energized (turned on) at step 222 at each set value. Then the program ends at step 224.

Thus, if it is detected that the engine 2 is started but not restarted, the heaters 142 are activated after the heater activation delay time (HDLY) that is a predetermined set time based on the engine water temperature. That is, the timing of the heater activation is set at the delay time based on the engine water temperature at the start of the engine. The start of the heater control is delayed from the start of the engine 2 according to the warm up of the engine 2, not based on the engine water temperature itself. Therefore, the oxygen sensors can be quickly activated without damage, and the feed back control for the air-fuel ratio can be achieved at an early stage to improve the purification of the exhaust gas by reducing the exhaust gas which is directly outputted to the environment.

In addition, if it is detected that the engine 2 is started and is restarted, the heaters 142 are activated at restart of the engine according to the duty value predetermined based on the engine water temperature. At the restart of the engine 2 in a state in which the engine is warmed up, the heater control can be immediately started since there is no damaging moisture in the oxygen sensors. The oxygen sensors can be quickly activated to improve purification of the exhaust gas.

Further, the restart determination section 66B determines that the engine 2 is restarted when the temperature differential between engine water temperature at the last engine stop and the engine water temperature at the next engine startup is less than a predetermined comparison temperature (e.g. 2° C.). The engine water temperature that is used for fuel injection control, is employed as a parameter to determine the restart of the engine 2, which simplifies the system.

Still further, the restart determination section 66B determines that the engine 2 is restarting if the elapsed time after the last engine stop is shorter than a predetermined comparison time (e.g. 10 minutes). Additional dedicated sensor to determinate the restart of the engine 2 can be eliminated, which simplifies the system and maintains the system compact.

Figure 13:
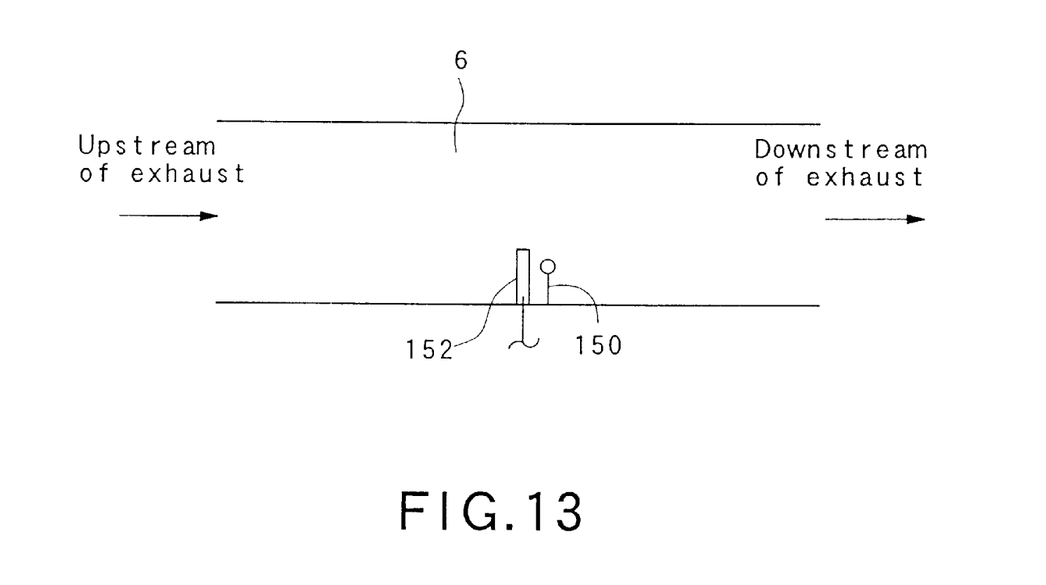
FIG. 13 is a schematic diagram showing a heater controller with a protection upstream of the oxygen sensor according to an embodiment of the invention.

FIG. 13 illustrates a further embodiment as a special configuration of the present invention. In this embodiment, the same functional parts are designated by the same reference numerals with respect to the above-described embodiment.

The configuration of FIG. 13 is characterized in that the oxygen sensor 150 in the exhaust passage 6 is provided with an upstream protection device 152 so as to cover the oxygen sensor 150. The protection device 152 is comprised of, e.g., a net member and serves as a heater and is controlled by the controller (not shown in FIG. 13).

According to this configuration, the moisture of the exhaust system coming from upstream of the exhaust flow contacts the protection device 152 to prevent the oxygen sensor 150 from contact with moisture as much as possible. Also, by heating the protection device 152 for a certain period when the temperature of the engine 2 at start up is at low, the protection device 152 evaporates the moisture deposited thereto. Thereby, the deposit of moisture onto the oxygen sensor 150 can be prevented to protect the oxygen sensor 150. After the certain time period is elapsed wherein the engine water temperature rises to a certain value, the heating of the protection device 152 may be stopped to avoid excess heating control.

The present invention is not limited to the above embodiments, but is susceptible to various applications, changes, and modifications which fall within the scope of the invention as described herein.

The control of the invention can be applied to, e.g., control of catalyst with the heater irrespective of the kinds of oxygen (exhaust) sensors. The heater activation delay time, the initial heater activation duty value (%), and the heater activation duty value (%) after elapsing of the heater activation time (AFHSTM) can be applied to the temperature of an engine part other than the engine water temperature, that can be detected during the engine warm up state.

As thus described, the present invention provides a controller and control method that includes a start detect section, a restart determination section, and a heater delay control section. The start detect section detects whether the engine is started. The restart determination section determines whether the engine is restarted. The heater delay control section operates the heater to activate after a predetermined delay time, delayed from startup of the engine, that is set according to an engine water temperature. The operation of the heater is executed when the start detect section detects that the engine is started and the restart determination section determines that the engine is not restarted. Accordingly, the heater is activated after the predetermined delay time that is set according to the engine water temperature at startup of the engine. Start of the heater control is delayed from the startup of the engine, which can be set not according to the engine water temperature but to a warm up state of the engine. The activation of the oxygen sensor is achieved at an early stage without damaging the sensor. The feed back control of the air-fuel ratio is achieved at an early stage to prevent increases in the exhaust output to improve the efficiency of exhaust gas purification.

Reference herein to "engine water temperature" will be understood to refer to the engine coolant temperature since the "coolant" is often referred to as "water" even though other liquids may be mixed therewith.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A heater controller for controlling the duty of a heater for an oxygen sensor which detects concentration of oxygen in exhaust gas of a vehicle engine, said controller comprising:
   a start detect section which detects whether said engine is started;
   a restart determination section which determines whether said engine is restarted; and
   a heater delay control section which operates to activate said heater after a predetermined delay time from startup of said engine and is set according to the engine coolant temperature;
   whereby said operation of said heater is executed when (1) said start detect section detects that said engine is started and (2) said restart determination section determines that said engine is not restarted.

2. The heater controller as defined in claim 1, wherein said restart determination section determines that the engine is restarted when the temperature differential between the engine coolant temperature at the last engine stop and the engine coolant temperature at the current engine startup is less than a predetermined comparison temperature.

3. The heater controller as defined in claim 2, wherein said predetermined comparison temperature is about 2° C.

4. The heater controller as defined in claim 1, wherein said restart determination section determines that the engine is restarted when the elapsed time after the last engine stop is shorter than a predetermined comparison time.

5. The heater controller as defined in claim 4, wherein said predetermined comparison time is about 10 minutes.

6. A heater controller for controlling the duty of a heater for an oxygen sensor which detects concentration of oxygen in exhaust gas of a vehicle engine, said controller comprising:
- a start detect section which detects whether said engine is started;
- a restart determination section which determines whether said engine is restarted; and
- a heater control section which operates to activate said heater at restart of said engine at a predetermined duty value according to engine coolant temperature;
- whereby operation of said heater is executed when said start detect section detects that said engine is started and said restart determination section determines that said engine is restarted.

7. The heater controller as defined in claim 6, wherein said restart determination section determines that the engine is restarted when the temperature differential between the engine coolant temperature at the last engine stop and the engine coolant temperature at the current engine startup is less than a predetermined comparison temperature.

8. The heater controller as defined in claim 7, wherein said predetermined comparison temperature is about 2° C.

9. The heater controller as defined in claim 6, wherein said restart determination section determines that the engine is restarted when the elapsed time after the last engine stop is shorter than a predetermined comparison time.

10. The heater controller as defined in claim 9, wherein said predetermined comparison time is about 10 minutes.

11. An internal combustion engine for a vehicle having an exhaust system defining an exhaust passage extending downstream from a combustion chamber, a feedback passage for controlled feedback of exhaust gas from the exhaust passage to an intake passage which supplies the combustion chamber, an oxygen sensor associated with the exhaust passage, a heater for heating the sensor, and a controller for controlling energization of the heater, the controller comprising:
- a start detection section which determines if the engine is started;
- a restart determination section which determines if the engine is restarted within a predetermined condition after the last stoppage of the engine;
- said controller, if it determines that the engine is started and also constitutes a restart, then immediately activating the heater at a predetermined energization level based on engine coolant temperature; and
- said controller, if it determines that the engine is started and does not constitute a restart, then activating the heater at an energy level based on engine coolant temperature but only after a predetermined time delay.

12. An engine according to claim 11, wherein the predetermined time delay is determined based on the engine coolant temperature at startup of the engine.

13. The engine as defined in claim 11, wherein said restart determination section determines that the engine is restarted when a temperature differential between engine coolant temperature at the last engine stop and the engine coolant temperature at engine startup is less than a predetermined comparison temperature.

14. The engine as defined in claim 11, wherein said restart determination section determines that the engine is restarted when the elapsed time after the last engine stop and the current startup is shorter than a predetermined comparison time.

15. A method to control a heater for an oxygen sensor that detects the oxygen concentration in the exhaust of an internal combustion engine, comprising the steps:
- detecting if the engine is started;
- determining if certain engine operational conditions exist to define that the engine is restarted;
- setting a heater activation delay time according to an engine coolant temperature if it is determined that the engine is started but not restarted; and
- setting a heater activation duty value according to an engine coolant temperature if it is detected that the engine is started and the engine is restarted.

16. The method of claim 15 further comprising the step of determining a temperature difference between an engine coolant temperature at the last engine stop and the engine coolant temperature at the current engine startup, and
- wherein the step of determining that said certain engine operational conditions exist to define that the engine is restarted comprises determining if said temperature difference is less than a certain temperature.

17. The method of claim 16 wherein said certain temperature is about 2° C.

18. The method of claim 15 further including the step of determining a time difference between the time of the last engine stop and the time of the current engine startup, and
- wherein the step of determining that said certain engine operational conditions exist to define that the engine is restarted comprises determining if said time difference is less than a certain time.

19. The method of claim 18, wherein said certain time is about 10 minutes.

20. A method of claim 15 setting the heater activation duty value according to engine coolant temperature after the setting of said heater activation delay time.

21. A method to control a heater for an oxygen sensor that detects the oxygen concentration in the exhaust of an internal combustion engine, comprising the steps:
- detecting if the engine is started;
- determining if certain engine operational conditions exist to define that the engine is restarted;
- setting a heater activation delay time according to an engine coolant temperature if the engine is started, but not restarted; and
- setting a heater activation duty value according to said engine coolant temperature if either (1) the engine is started and restarted, or (2) after setting of said heater activation delay time.

22. The method of claim 21 further including the step of determining a temperature difference between the engine coolant temperature at the last engine stop and the engine coolant temperature at the current engine startup, and
- wherein the step of determining that said certain engine operational conditions exist to define that the engine is restarted comprises determining if said temperature difference is less than a certain temperature.

23. The method of claim 22, wherein said certain temperature is about 2° C.

24. The method of claim 21 further including the step of determining a time difference between the time of the last engine stop and the time of the current engine startup, and
- wherein the step of determining that said certain engine operational conditions exist to define that the engine is restarted comprises determining if said time difference is less than a certain time.

25. The method of claim 24, wherein said certain time is about 10 minutes.

* * * * *